United States Patent [19]
Rudisill et al.

[11] Patent Number: 5,544,530
[45] Date of Patent: Aug. 13, 1996

[54] ASSEMBLY SUITABLE FOR LIFE TESTING A MULTI-DIMENSIONAL FORCE TRANSDUCER

[75] Inventors: Charles A. Rudisill, Apex, N.C.; Joseph D. Rutledge, Mahopac, N.Y.; Edwin J. Selker, Palo Alto, Calif.

[73] Assignee: International Business Machines Corporation, Armonk, N.Y.

[21] Appl. No.: 330,878

[22] Filed: Oct. 28, 1994

[51] Int. Cl.$^6$ .................................................. G01N 3/32
[52] U.S. Cl. ............................................. 73/810; 73/811
[58] Field of Search ............................ 73/1 B, 808, 810, 73/813, 811

[56] References Cited

U.S. PATENT DOCUMENTS 2,789,427  4/1957  Brier ........................................ 73/1 B
3,585,840  9/1969  Landsness ................................ 73/1 B
5,020,357  6/1991  Kovacevic et al. ..................... 73/1 B Primary Examiner—Hezron E. Williams
Assistant Examiner—Nashmiya Ashraf
Attorney, Agent, or Firm—Stephen C. Kaufman; Ronald L. Drumheller

[57] ABSTRACT

A test assembly suitable for life testing a computer pointing stick includes a rigid shaft that is rotated by a motor and a mounting mechanism for holding and positioning the pointing stick under test in a coaxial relationship with the rigid shaft. A cantilever spring arm is rigidly connected at one end to the rigid shaft so that it rotates with the rigid shaft and is mechanically coupled under lateral spring tension at its other end to the pointing stick. The spring rotates with the rigid shaft and applies lateral force to the pointing stick via a collar attached to the pointing stick, the direction of the applied force rotating with the rigid shaft and cantilever spring. A counter records the cumulative number of flexure cycles required to make the pointing stick functionally fail.

5 Claims, 2 Drawing Sheets

ASSEMBLY SUITABLE FOR LIFE TESTING A MULTI-DIMENSIONAL FORCE TRANSDUCER

BACKGROUND OF THE INVENTION

This invention relates to an assembly suitable for carrying out life testing of a multi-dimensional force transducer.

INTRODUCTION TO THE INVENTION

We are manufacturing laptop computers, wherein associated computer interfaces preferably utilize a pointing stick as an advantageous alternative to a conventional mouse.

In overview, and with respect to functionality, the pointing stick comprises an input device that can be used by a human operator in conjunction with the keys of a keyboard of a laptop computer, in order to enter data into the computer. For example, in response and in correspondence to an operator's mechanical force input to the pointing stick, the computer can respond by moving a cursor around a computer screen.

In particular, a typical pointing stick can function as an analog transducer for translating a mechanical force input into output electrical signals that reflect the components of the mechanical force input in two or more dimensions (e.g., cursor movement in X, Y and Z directions).

With respect to structure, a typical such pointing stick that we manufacture preferably comprises a plastic shaft 0.140" square and 9 mm length, integral with a base designed for insertion into the keyboard. A section near the base preferably has orthogonal fiats to which conventional strain gauges may be bonded. In operation, the pointing stick typically responds to a maximal normal force (say 0–350 grams) by movement within approximately 0.008 inch.

SUMMARY OF THE INVENTION

Our work includes conceptualizing and generating viable manufacturing designs for such force transducers—pointing sticks (devices). By a viable manufacturing design, we mean firstly, one that can meet the adumbrated functional and structural metrics for a device. Secondly, a viable design ensures that a device can realize a projected life i.e., that the device can maintain a constant transfer function (force to voltage) throughout a life of millions of cycles of flexures.

Our work may be restated in the following way. Assume that a device design is not viable. For example, it may be the case that a device under a life test can not respond accurately to applied force in a predetermined manner over a long period of time, say due to inter alia the strain gauge bonds breaking, or the plastic shaft breaking or deteriorating. For this situation, accordingly, it is imperative that the information and knowledge about the inadequacy of the device design, as supplied by way of the life test, be itself accurate and derivable from a simple and durable life testing mechanism.

We have now discovered a novel life test assembly that can simulate the flexure activity (approximately $10^7$ flexures) in a reasonable time, under controlled conditions and with continuous monitoring. These advantages may be realized in a test assembly comprising:

1) a mounting mechanism for holding and positioning a force transducer under test;
2) a transducer so mounted in the mounting mechanism and comprising an accessible sensing member;
3) a rigid shaft which can be rotated at a controllable speed;
4) a cantilever spring rigidly connected at one end to the rigid shaft and connected at its other end to the transducer sensing member so that the spring can rotate with the rigid shaft while remaining in contact with the sensing member; and
5) a counter for recording a cumulative number of rotations of the rigid shaft.

The invention as defined can realize important advantages, since a robust and efficient assembly may be readily and inexpensively created from conventional components (given the disclosure, below).

BRIEF DESCRIPTION OF THE DRAWING

The invention is illustrated in the accompanying drawing, in which.

DETAILED DESCRIPTION OF THE INVENTION

Figure 1:
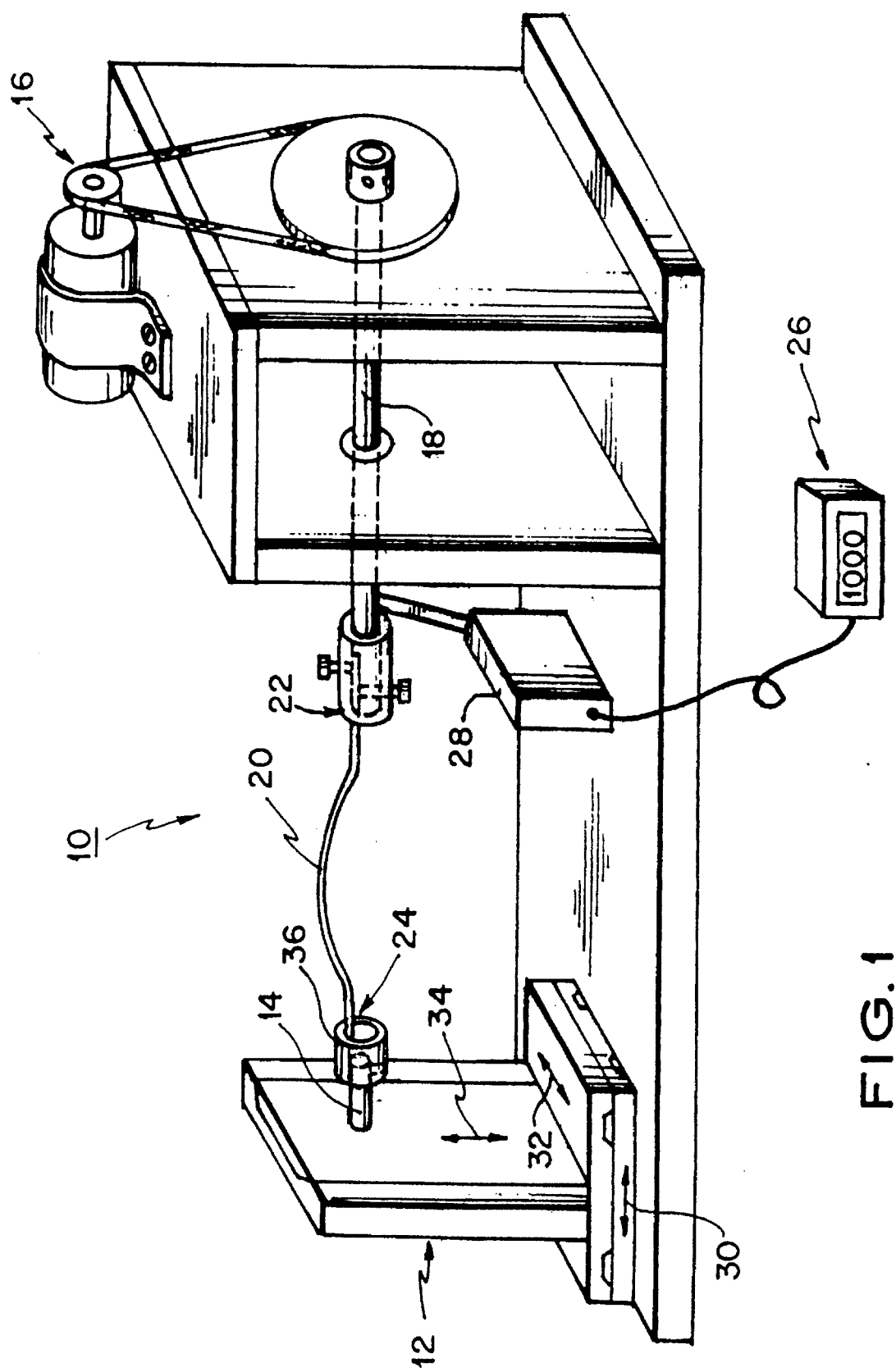
FIG. 1 shows a test assembly of the present invention.

Attention is now directed to FIG. 1, which shows a preferred embodiment of a test assembly 10 of the present invention.

In overview, the test assembly 10 comprises a mounting mechanism 12 for holding and positioning a force transducer 14 under test, a motor/pulley arrangement 16 comprising a rotatable rigid shaft 18, a cantilever spring 20 rigidly connected (by way of a set screw) at one end 22 to the rigid shaft 18 and connected at its other end 24 to a sensing member of tile force transducer 14, and a counter 26 and associated micro-switch 28 in operative association with the rigid shaft 18. Conventional elements are suitable for realizing this embodiment. A purpose of the FIG. 1 test assembly 10 is for applying a controlled force of constant magnitude and varying direction to the test force transducer 14. For example, a requirement of a suitable life test may be to apply a controlled force to the force transducer 14 cyclically and in all directions in the horizontal plane.

To this end, the force transducer 14 preferably is mounted with an axis of its sensing member colinear with the rotating shaft 18. To accommodate this action, the mounting mechanism 12 may be selectively positioned in X, Y and Z directions (see arrows 30, 32, 34).

As noted, the cantilever spring 20 is connected at one end 22 to the rigid shaft 18, and connected at its other end 24 to the sensing member of the force transducer 14. These connections can be realized in various ways.

For example, the cantilever spring 20 preferably comprises a high-compliance elastic member to apply a requisite force to the sensing member and realize substantial immunity from alignment or positioning errors. In the FIG. 1 variation, a more or less tubular collar 36 preferably is attached in a conventional manner to the sensing member, so that one end of the cantilever spring 20 is constrained to slide inside the collar 36. At the same time, the other end of the cantilever spring 20 is mounted to the rigid shaft 18 at an angle Ø, so that force is required to bring the end of the cantilever spring 20 to an extended center line of the rigid shaft 18. Accordingly, when the rigid shaft 18 rotates, a force with constant magnitude depending on the angle Ø, and direction rotating with the rigid shaft 18, is applied to the collar 36 and thus to the force transducer 14.

Note that by properly choosing the properties of the cantilever spring 20, the force applied to the collar 36 can be made relatively insensitive to the exact dimensions of the collar 36, and to the exact alignment of the axes of rigid shaft 18 and force transducer 14. The only sliding bearing is between the rigid shaft 18 and the collar 36. Preferably, the collar 36 comprises Teflon e.g., it is self-lubricating and can have a reasonably long life, typically above $2\times10^7$ cycles (flexures), or several weeks of continuous running. Note further that the exact force applied is most easily measured directly by the output of the force transducer under test, and symmetry may be easily measured and adjusted.

Figure 2:
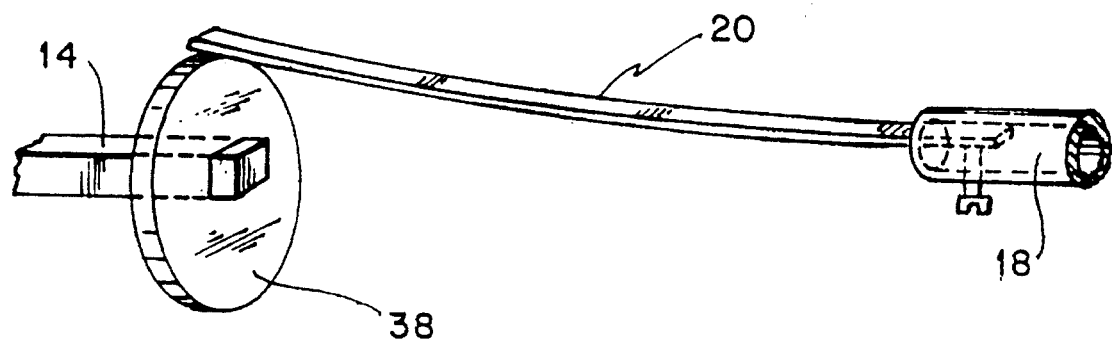
FIG. 2 shows details of one embodiment of the present invention.

A FIG. 2 variation to the FIG. 1 embodiment is invarient, mutatis mutandis, except a disk-shaped collar 38 preferably is attached to the force transducer 14 so that one end of the cantilever spring 20 bears against its rim and is thus forced away from an axis of the rigid shaft 18. At the same time, the other end of the cantilever spring 20 preferably is mounted coaxially with the rigid shaft 18, principally flexible in one direction, so that when the rigid shaft 18 rotates, a force depending on the radius of the collar 38, and direction rotating with the rigid shaft 18, is applied to the collar 38 anti thus to the force transducer 14.

EXAMPLE

A test assembly was built in accordance with the present invention. The specifications were as follows.

The rigid shaft was ¼" steel, with ball bearings in Lucite blocks, mounted on a 1" thick plywood base. The driving motor was a sewing machine motor, having a range of 10 to 100 cycles per second, mounted above the rigid shaft. The force transducer under test comprised a pointing stick mounted on a three dimensional stage, with adjustment by simple sliding with locking screws. The cantilever spring comprised 5" length of 1/16" music wire. It was anchored in a Delrin cylinder on the end of the rigid shaft, with several set screws which both anchored it and controlled its angle with respect to the rigid shaft, and thus the force applied to the pointing stick. The design of the pointing stick was thus enabled to be tested for sustaining on the order of $10^7$ flexures during its operating life, without appreciable changes in its characteristics. The testing was done in a reasonable time, under controlled conditions, and with continuous monitoring.

What is claimed:

1. A test assembly for mechanically cycling a multi-dimensional force transducer through all directions of lateral deflection of a sensing member until the force transducer functionally fails, comprising:
   1) a rigid shaft;
   2) a mounting mechanism for holding and positioning a force transducer under test, said force transducer having such sensing member defining an axis with respect to which lateral forces applied to said sensing member are sensed, said mounting mechanism positioning said sensing member and said rigid shaft coaxially along a common axis;
   3) a motor for rotating said rigid shaft;
   4) a cantilever spring having first and second ends, said first end being rigidly connected to the rigid shaft and said second end being mechanically coupled to the sensing member under lateral spring tension so that the cantilever spring can rotate with the rigid shaft while applying a lateral force to the sensing member, the applied lateral force rotating in direction with the rigid shaft; and
   5) a counter for recording a cumulative number of rotations of the rigid shaft until the force transducer functionally fails.

2. An assembly according to claim 1, wherein the cantilever spring is rigidly connected at said first end to the rigid shaft at a controllable angle for applying a controlled amount of lateral spring tension force to the sensing member.

3. A test assembly according to claim 1, wherein
   1) a collar is attached to the sensing member; and
   2) the spring contacts the collar as a bearing on an inside surface of the collar, so that the spring exerts a force on the collar in a direction away from said common axis.

4. A test assembly according to claim 1, wherein
   1) a collar is attached to the sensing member; and
   2) the spring externally contacts the collar, so as to apply a force to the collar towards said common axis.

5. An assembly according to claim 1, wherein the rigid shaft is rotated by the motor at a speed of from 10 to 100 cycles per second.

* * * * *